United States Patent [19]

Arbogast et al.

[11] 4,177,525
[45] Dec. 11, 1979

[54] REINFORCED ARTIFICIAL FOOT AND METHOD OF MAKING

[75] Inventors: Charles J. Arbogast; Robert E. Arbogast, both of Mount Sterling, Ohio

[73] Assignee: Ohio Willow Wood Co., Inc., Mount Sterling, Ohio

[21] Appl. No.: 849,763

[22] Filed: Nov. 9, 1977

[51] Int. Cl.² ............................................. A61F 1/08
[52] U.S. Cl. ......................................... 3/7; 264/46.7
[58] Field of Search ................ 3/6, 6.1, 7, 30, 32, 3/33; 264/46.7

[56] References Cited

U.S. PATENT DOCUMENTS

| | | | |
|---|---|---|---|
| 2,551,724 | 5/1951 | Campbell | 3/7 X |
| 2,556,525 | 6/1951 | Drennon | 3/6.1 X |
| 3,335,428 | 8/1967 | Gajdos | 3/7 |
| 3,833,941 | 9/1974 | Wagner | 3/7 |
| 3,890,650 | 6/1975 | Prahl | 3/7 |

FOREIGN PATENT DOCUMENTS

| | | | |
|---|---|---|---|
| 1371996 | 10/1974 | United Kingdom | 3/7 |
| 1434413 | 5/1976 | United Kingdom | 3/7 |

Primary Examiner—Clifford D. Crowder
Attorney, Agent, or Firm—Francis T. Kremblas, Jr.; Frank H. Foster

[57] ABSTRACT

An improved construction and method of making an artificial foot characterized by a rigid keel portion comprising a molded plastic material having a metal reinforcing strip imbedded within said plastic keel portion near the lower surface thereof. This keel portion is surrounded by a typical flexible foamed plastic material molded to said keel to form the outer surface of the foot. Preferably the reinforcing strip includes a metal receiver fixed to the strip and also is imbedded within the rigid keel to receive connecting means to attach the foot to the remainder of the prosthetic leg portion.

15 Claims, 2 Drawing Figures

REINFORCED ARTIFICIAL FOOT AND METHOD OF MAKING

BACKGROUND OF PRESENT INVENTION

Prior to 1960 most artifical feet were made from solid wood with a series of hinge or pivot points utilized to simulate natural foot movement. Upon the introduction of so-called one-piece SACH type foot construction which utilized a rigid core or keel portion surrounded by a molded flexible, polyurethane covering, many of the adverse problems of the prior constructions were improved. However, this construction also created a new set of problems, most of which related to the rigid core which consisted of wood or metal. Although many attempts have been made to improve this type of construction, most artifical feet manufactured up to the present use of wood core or keel since the metal keels were found to be even more unsatisfactory.

For example, the metal keels generally proved to be heavier than desirable and were even more difficult to bond well to the polyurethane outer cover surface than wooden keels. Insufficient bonding at the interface between the core and outer covering leads to early failures.

However, improved as it was over the much earlier constructions, the wood keel construction and molded flexible outer cover have been much less than satisfactory for many reasons.

First, wood cores must be hand crafted which fails to achieve a desirable level of uniformity and increases the cost of manufacture.

Second, inherently wood is subject to non-uniformity in grain structure, mineral streaks, etc., such that individual testing is required which further increases costs.

Third, it is very important to maintain the wood keel moisture free to ensure strength and to obtain at least reasonable bonding to the polyurethane outer surface. The tendency of wood to absorb moisture makes control of this variable difficult and costly.

Fourth, polyurethanes do not bond as well as desired to dissimilar materials, such as wood, and therefore even under ideal conditions, the bonding interface is subject to more than a reasonable number of failures which shortens useful life.

Further, since failures and long life are not the rule with prior art type artifical feet, a rather simple means of connection must be employed to permit easy replacement. Typically a bolt is inserted through the keel which is also attached to the artifical leg portion. Therefore as a wood keel expands and contracts with climatic changes and through the natural forces encountered during use, a loss of torque of the attaching bolt occurs. This results in dangerous as well as embarrassing rotation of the foot relative to the upper portion of the leg.

In spite of all of these problems, the wooden keel type construction still dominates the industry and many prior attempts to improve these drawbacks have failed or lead to problems of equal or more serious dimensions.

For example, one suggested solution was substitution of a metal plate, aluminum, for example, for the entire keel with the flexible polyurethane molded around it. However, since this plate is subject to relatively high bending movements, thickness was required which resulted in added weight. Increased weight at this point so far from the knee center of an artifical leg results in an increased moment about the knee hinging point and causes an undesirable stress on control mechanisms which regulate the flexion and extension of the shin portion relative to the thigh. In addition, added weight in this portion of the foot causes an undesirable increase in terminal impact upon full extension of the shin.

A further disadvantage to this construction, which is disclosed in U.S. Pat. No 3,890,650, is that the void above the metal plate must be filled with a material of sufficient strength to cope with the high forces generated at the attaching point of the foot to the artifical leg. This again adds more weight and increases the detrimental results mentioned above. Also, it should be noted that this construction requires a surface bond between a non-porous material, the metal plate, to the flexible urethane. Such a bond is notoriously subject to failure and results in a short useful life of the product.

Other examples of attempts to solve the problems encountered with the manufacture of artifical feet are represented by U.S. Pat. Nos. 3,098,239; 3,484,871; 3,766,569; 3,833,941; 3,920,610 and 3,874,004.

SUMMARY OF THE PRESENT INVENTION

The present invention relates generally to the manufacture of artifical feet and particularly to a method and construction of an improved artifical foot which solves many of the problems which heretofore appeared to be inherently inexcapable in many prior art constructions because of the seemingly contradictory requirements of an ideal foot construction.

The artifical foot of the present invention provides a keel comprising a foamed urethane which becomes rigid upon curing which is molded with a reinforcing strip placed in the mold to form a unitary structure which has excellent strength properties and is lighter in weight than wood.

In the preferred keel structure, the reinforcing stip includes a metal receiver for the attaching bolt which itself is also imbedded within the molded rigid urethane keel.

The metal reinforcing strip is disposed near the bottom surface of rigid urethane keel and is provided with a series of holes through which the rigid urethane fills during the molding step to more securely hold the strip in position.

This keel is then placed in another suitable mold wherein the typical flexible polyurethane is poured to form the outer covering having the contour of a human foot. Since the keel comprises a porous polyurethane foam, the flexible outer covering bonds extremely well to the rigid, porous polyurethane keel along the interface.

In this manner, the present invention enhances the desirable characteristics of less weight as compared to wood with greater strength under both compression and tensile forces and excellent impact resistance to provide longer useful life while retaining the other desirable features of the SACH type foot.

OBJECTS OF THE PRESENT INVENTION

It is a primary object of the present invention to provide a novel artifical foot construction which reduces or eliminates the undesirable characteristics associated with prior art constructions and yet is not of unreasonable cost to the intended user.

It is another object of the present invention to provide an artifical foot of the type described which includes a unique keel construction which is at least as light or lighter in weight than typical wooden keels and yet has improved strength characteristics compared to such prior art type keels.

It is another object of the present invention to provide an artifical foot of the type described in which the material comprising the keel portion permits a dramatically improved bond to be formed at the interface between the flexible polyurethane outer covering to reduce the failures due to separation of the various layers comprising the foot construction.

It is still another object of the present invention to provide an artifical foot which is well-suited for automated production to enhance consistentcy of quality at reduced costs.

It is a further object of the present invention to provide an artifical foot in which the keel portion exhibits low moisture absorbtion rates as compared to wood yet exhibits much greater compression resistance at the attaching point of the artifical leg and greater impact resistance at the ball of the foot while not increasing the overall weight compared to the most popular type of prior art artifical feet presently being used.

Further objects and features of the invention will be apparent from the following specification and claims when considered in connection with the accompanying drawings illustrating several embodiments of the invention.

IN THE DRAWINGS

DETAILED DESCRIPTION OF PRESENT INVENTION

Figure 1:
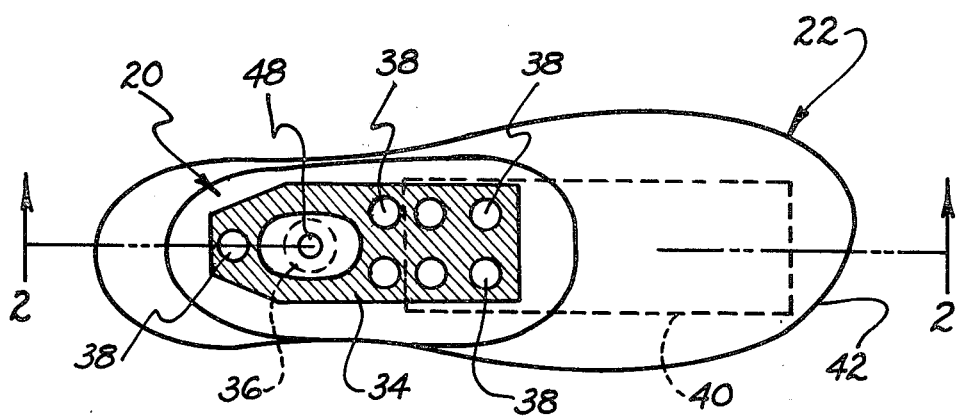
FIG. 1 is a top plan view in section of an artifical foot made in accordance with the present invention, with the section being taken along line 1—1 in FIG. 2.
Figure 2:
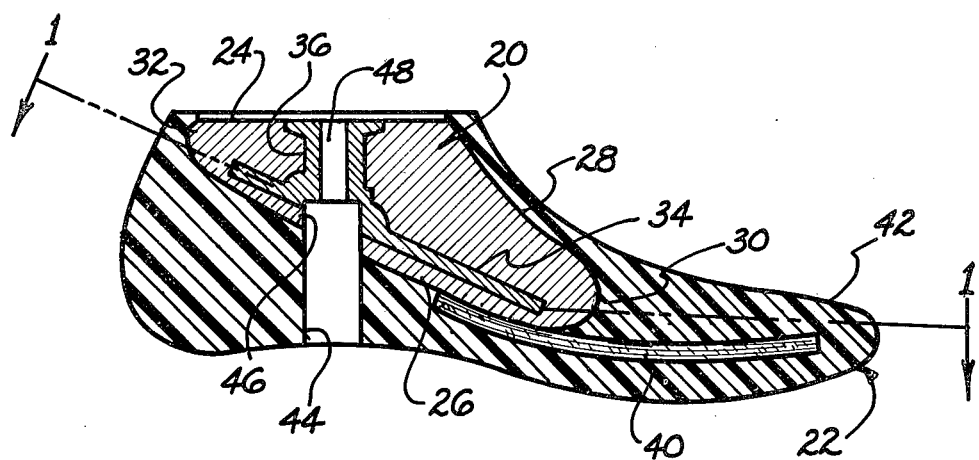
FIG. 2 is a side elevational view in section of the foot shown in FIG. 1, with the section being taken along line 2—2 of FIG. 1.

Referring in detail to the drawing, an artifical foot constructed in accordance with the present invention is illustrated in FIGS. 1 and 2 and includes a rigid keel portion, indicated generally at 20, and a flexible outer covering, indicated generally at 22, which conforms generally to the shape of a human foot.

Keel portion 20 and outer covering 22 are manufactured in a molded fashion to effectively provide a unitary structure upon completion of manufacture.

Keel 20 comprises a rigid, porous material, preferably one of the polyurethanes, which is foamable to form an open celled structure and yet becomes rigid upon curing. Such polyurethanes are well-known in the art. The overall shape of the keel 20 is similar to the shape of prior art keels in that it has a flat top protion 24, a flat, downwardly sloping arch portion 26 and a downwardly sloping, curved instep portion 28 and rounded front and rear end portions 30 and 32 respectively.

Molded within keel 20 is a metal reinforcing strip 34 and a metal bolt receiver 36 which is firmly fixed to strip 34 such as by welding or the like. It should be noted that strip 34 and receiver 36 may be cast in one piece if desired, without departing from the spirit of the present invention.

Reinforcing strip 34 and receiver 36 are preferably made of aluminum in order to maintain the overall weight of the foot as low as possible. However, it should be noted that strip 34 may be relatively thin, such as one-eighth of an inch in thickness, and still achieve the desirable results of improved strength accomplished in accordance with the teachings of the present invention.

Also reinforcing strip 34 is provided with a plurality of holes, such as 38, which permit the rigid urethane portion to pass through each hole during the molding step and more effectively secure the position of strip 34 upon curing. In effect, rigid polyurethane posts are integrally formed through holes 38 during the molding step.

After keel 20 is formed as described above, it is placed in another suitable mold and a flexible plastic material, preferably a typical foamable polyurethane formulation, is poured in the well-known manner to form outer covering portion 22. If desired, a strip of belting material 40 may conventionally be suitably placed under the forward end of keel 20 and extended forwardly toward the toe portions 42 to add a degree of stiffness to the flexible covering portion in that forward area of the foot.

Also, conventionally, a plug is employed to form a bore or hole 44 in the bottom of outer covering 22 which mates with a similar hole 46 originally provided in a similar manner in keel 20 and which is aligned with the hole 48 extending through receiver 36.

This provides means for fastening the foot to the bottom of the artifical leg by the conventional means of a bolt extending through hole 48 with holes 46 and 44 functioning as headholes for attaching a nut onto the bolt.

It is important to point out that in the use of a rigid porous, plastic material to form keel 20, the type and size of the reinforcing material is important but the positioning of the strip within the keel is critical to achieve the desired improvement in strength. After much experimenting and testing, including evenly distributing reinforcement material throughout the keel, excellent results were achieved only when the reinforcing strip was positioned to limit the ability of the bottom portion of keel 20 in the area of the arch to expand or resist tensile forces upon the application of bending moments such as encountered during normal use.

Since tests indicate the rigid polyurethane structure absorb compression forces quite well, it is theorized that the porous polyurethane keel without reinforcement in accordance with the invention failed regularly due to these tensile forces which occur upon the application of these bending moments. It can be shown that the lower cross-sectional half of the keel is in tension while the other half is in compression upon application of these bending moments. Therefore the placement of the strip 36 along most of the length and near the bottom surface 26 of keel 20 is extremely important in order to realize the full advantages and greatly improved characteristics of the present invention.

Other tests revealed that in the construction of the present invention resistance to compression forces at the attaching point to the remainder of the artifical leg is far greater than that of wood.

However, it should be noted that one may eliminate the metal receiver portion and utilize only the metallic strip portion without departing from the present invention and still provide a very much improved construction as compared to the prior art. The rigid polyurethane is at least favorably comparable to wood relative to resistance to compression forces at the attaching point of the bolt and the reinforcing strip provides a solution to the most troublesome problems heretofore encountered. It is believed however, that the embodiment described herein employing both the metal receiver and strip represents the most optimum construction for both manufacturing as well as performance efficiencies.

Utilizing this construction also permits these exellent improvements in strength and impact resistance to be achieved while maintaining the overall weight at generally ten percent less than comparable prior art constructions utilizing wooden keels.

Further, it should be pointed out that the porous, rigid plastic material of keel 20 possesses a significantly lower rate of moisture absorbtion than wooden keels and permits a stronger bond to be formed along the interface with the flexible outer covering which is typically a porous polyurethane.

In addition, it should be quite evident that the molding step used to form keel 20 is much more condusive to duplication of both shape and size and lends to greater consistency of quality compared to hand crafted wooden keels. Moled keels lend themselves to achieving high production rates and potential savings in labor costs.

The prosthetic industry has long become accustomed to a relatively short-life for artificl feet, six months to two years, for example. However, test results strongly indicated that feet constructed in accordance with the present invention will have significantly longer life and yet equal or improve the functional qualities compared to prior artifical feet.

What is claimed is:

1. An artifical foot comprising, in combination, a rigid keel portion comprising a porous plastic material disposed in the ankle region and having a flat top portion, a relatively flat, downwardly sloping bottom portion integrally formed with a curved instep portion and rounded toe and rear portions, said plastic material being molded in surrounding relationship to a metallic insert securely imbedded within said plastic material and including a vertical extending bolt receiver portion adapted to receive a fastener means and a flat elongate strip portion joined to said receiver portion, said strip portion disposed in the lower portion of said keel in generally parallel extending relationship to said sloping bottom portion thereof; and a flexible porous, plastic covering molded in surrounding and bonded relationship to said keel portion and having the general configuration of the human foot.

2. The artifical foot defined in claim 1 wherein said rigid plastic material of said keel portion is a foamed polyurethane.

3. The artifical foot defined in claim 1 wherein said flexible cover is a foamed polyurethane material.

4. The artifical foot defined in claim 1 wherein said flat, elongated metal strip imbedded within said keel portion includes a plurality of spaced holes having said plastic material forming said keel portion extending through said holes.

5. The artifical foot defined in claim 4, wherein both said rigid keel portion and said flexible covering comprise foamed polyurethane materials.

6. The artifical foot defined in claim 1 wherein said metallic insert is aluminum and said elongate strip portion is no greater than approximately one-eighth of an inch in nominal thickness and at least as wide as one-half the width of the said keel portion.

7. In a keel forming the ankle portion for use in making an artifical foot of the type having a flexible foamed plastic outer coating generally conforming to the shape of a human foot the combination of rigid, foamed plastic material molded in one-piece in surrounding relationship to a metallic insert, said metallic insert including a vertically extending bolt-receiver portion and a flat, elongate strip portion, said receiver portion adapted to receive a bolt fixing said foot to the remainder of an artifical leg and said strip portion positioned within said keel to reduce tensile forces applied along the bottom portion of said keel during the application of bending moments experienced during normal use.

8. The keel defined in claim 7 wherein said rigid foamed plastic material is a polyurethane.

9. The keel defined in claim 7 wherein said metallic strip portion includes a plurality of spaced holes filled with said molded rigid plastic material to securely fix said strip within said plastic material.

10. A method of making an artifical foot comprising the steps of molding a rigid porous keel portion from a foamed plastic material in surrounding relationship to a metallic insert having a vertically extending bolt receiver portion and a flat elongated strip portion, said strip portion positioned within said plastic keel to significantly reduce the ability of the bottom portion of said keel from expanding upon the application of a bending moment such as encountered during expected use; and molding a flexible foamed plastic covering in bonded and surrounding relationship to said plastic keel portion in the general form of a human foot.

11. The method defined in claim 10 wherein said porous foamed plastic material forming said keel comprises a polyurethane.

12. The method defined in claim 11 wherein said flexible covering comprises a polyurethane.

13. The method defined in claim 10 including the step of providing the strip portion of said metallic insert with a plurality of spaced holes prior to molding said rigid, foam plastic material in surrounding relationship to said insert.

14. An artifical foot comprising in combination, a rigid keel portion comprising a rigid porous plastic material disposed in the ankle region and having a flat top portion, a relatively downwardly curved instep portion, a sloping bottom portion, and rounded toe and heel portion, said plastic material being molded in completely surrounding relationship to a metallic reinforcing strip securely imbedded within said plastic material, and disposed in the lower portion of said keel portion adjacent to and in generally parallel extending relationship along substantially the length of said sloping bottom portion thereof, and a flexible porous plastic covering molded in surrounding and bonded relationship to said keel portion and having the general configuration of the human foot.

15. The artifical foot defined in claim 14 wherein said metallic strip includes a plurality of spaced holes and said molded plastic material extends in a continuous manner through said holes to securely fix the position of said strip.

* * * * *